United States Patent
Hasegawa et al.

(10) Patent No.: US 8,529,519 B2
(45) Date of Patent: Sep. 10, 2013

(54) TIGHT-SEALING CAP FOR LIQUID DRUG-EXPELLING PART

(75) Inventors: Mitsuru Hasegawa, Tokyo (JP); Taiji Horita, Osaka (JP)

(73) Assignees: Seikagaku Corporation (JP); Taisei Kako Co., Ltd. (JP)

(*) Notice: Subject to any disclaimer, the term of this patent is extended or adjusted under 35 U.S.C. 154(b) by 150 days.

(21) Appl. No.: 12/935,638

(22) PCT Filed: Mar. 30, 2009

(86) PCT No.: PCT/JP2009/056565
§ 371 (c)(1),
(2), (4) Date: Jan. 5, 2011

(87) PCT Pub. No.: WO2009/123150
PCT Pub. Date: Oct. 8, 2009

(65) Prior Publication Data
US 2011/0139830 A1   Jun. 16, 2011

(30) Foreign Application Priority Data
Apr. 1, 2008   (JP) .................................. 2008-094641

(51) Int. Cl.
*A61M 5/32*   (2006.01)
(52) U.S. Cl.
USPC ........................................................ 604/199
(58) Field of Classification Search
USPC ................................................. 604/187, 199
See application file for complete search history.

(56) References Cited

U.S. PATENT DOCUMENTS

| 4,628,969 A | 12/1986 | Jurgens, Jr. et al. |
| 4,723,945 A | 2/1988 | Theiling |

(Continued)

FOREIGN PATENT DOCUMENTS

| EP | 0505579 A1 | 9/1992 |
| JP | 50-039953 A | 4/1975 |

(Continued)

OTHER PUBLICATIONS

International Search Report, PCT/JP2009/056565, dated Jun. 23, 2009.

(Continued)

*Primary Examiner* — Victoria P Shumate
(74) *Attorney, Agent, or Firm* — Lerner, David, Littenberg, Krumholz & Mentlik, LLP

(57) ABSTRACT

Provided is a tight-sealing cap for the liquid drug-expelling part of a syringe that not only minimizes the space that creates reduced pressure, which is a cause of leakage, but is also easy to remove because it is easily twisted off, easily deformable and easily admits air for releasing the vacuum when removed, and that can prevent leaking of a liquid drug from a luer nozzle. The cap is made of an elastic material, and the following means are used in the cap, which is configured from a thick upper surface part, an outer tubular part that is formed below the periphery thereof, and an inner tubular part that is formed inside the same. First, the inner tubular part is formed so that the tip of the luer nozzle can be inserted tightly into the same, and the luer nozzle can be tightly sealed at the site of contact thereof. Second, the outer tubular part is formed so that it contacts the luer lock closely therein and can seal the luer lock tightly at the site of contact thereof. Third, the length of the site of contact between the outer tubular part and the luer lock is shorter than the length of the site of contact between the inner tubular part and the luer nozzle.

4 Claims, 4 Drawing Sheets

(56) References Cited

U.S. PATENT DOCUMENTS

| | | |
|---|---|---|
| 5,489,266 A | 2/1996 | Grimard |
| 5,624,402 A | 4/1997 | Imbert |
| 6,090,081 A | 7/2000 | Sudo et al. |
| 6,129,711 A | 10/2000 | Speck |
| 6,162,200 A * | 12/2000 | Sawa et al. .................. 604/230 |
| 2002/0022809 A1 | 2/2002 | Sudo et al. |
| 2003/0034264 A1 | 2/2003 | Hamai et al. |
| 2004/0039341 A1* | 2/2004 | Ranalletta .................. 604/199 |
| 2004/0122374 A1* | 6/2004 | Hasegawa .................. 604/187 |
| 2004/0133169 A1* | 7/2004 | Heinz et al. .................. 604/187 |
| 2007/0100294 A1 | 5/2007 | Sugita et al. |
| 2007/0260189 A1* | 11/2007 | Shaw et al. .................. 604/187 |
| 2007/0287965 A1* | 12/2007 | Strong et al. .................. 604/218 |
| 2008/0132851 A1* | 6/2008 | Shaw et al. .................. 604/199 |
| 2008/0215012 A1* | 9/2008 | Horita et al. .................. 604/191 |
| 2011/0139830 A1* | 6/2011 | Hasegawa et al. .......... 222/562 |

FOREIGN PATENT DOCUMENTS

| | | |
|---|---|---|
| JP | 62-194866 A | 8/1987 |
| JP | 04-150868 A | 5/1992 |
| JP | 05-305140 A | 11/1993 |
| JP | 06-066692 A | 3/1994 |
| JP | 06-254161 A | 9/1994 |
| JP | 07-213608 A | 8/1995 |
| JP | 08-215307 A | 8/1996 |
| JP | 09-028798 A | 2/1997 |
| JP | 10-507670 T | 7/1998 |
| JP | 10-248929 A | 9/1998 |
| JP | 10-314305 A | 12/1998 |
| JP | 2000-157630 A | 6/2000 |
| JP | 2002-143301 A | 5/2002 |
| JP | 2002-153539 A | 5/2002 |
| JP | 2002-177395 A | 6/2002 |
| JP | 2002-210008 A | 7/2002 |
| JP | 2002-210011 A | 7/2002 |
| JP | 2003-052819 A | 2/2003 |
| JP | 2006-006791 A | 1/2006 |
| JP | 2006230739 A | 9/2006 |
| JP | 2007-117379 A | 5/2007 |
| JP | 2007-275305 A | 10/2007 |
| JP | 2007-536060 T | 12/2007 |
| WO | 2005/113038 A2 | 12/2005 |

OTHER PUBLICATIONS

International Preliminary Report on Patentability, PCT/JP2009/056565, dated Dec. 9, 2010.

* cited by examiner

TIGHT-SEALING CAP FOR LIQUID DRUG-EXPELLING PART

TECHNICAL FIELD

The present invention relates to improvements of a tight-sealing cap for liquid drug-expelling part and particularly relates to improvements of a cap made of an elastic material for tightly sealing a liquid drug-expelling part of a syringe-cum-container (hereinafter referred to as a "syringe") in which part a tubular luer lock part stands to surround a luer nozzle with a space between an inner surface of the tubular luer lock part and an outer surface of the luer nozzle.

BACKGROUND ART

So far, a cap, which is what might be called an "overcap", is attached to a liquid drug-expelling part in order to prevent vapor or moisture from entering into the liquid drug-expelling part when a syringe is sterilized by heating as is disclosed in the Patent Document 1.

A cap of this kind (referred to as a "nozzle cap" in the Patent Document 1) comprises a top surface portion that makes an external form, an outer tubular part that is formed below the outer periphery thereof to tightly seal a luer lock part and an inner tubular part that is formed below the top surface part on the inside thereof to tightly seal a luer nozzle. Then, as is disclosed in the Patent Document 1, it is customary that the length of the outer tubular part that tightly seals the luer lock part is longer than the length of the inner tubular part that tightly seals the luer nozzle part.

If the outer tubular part that tightly seals this luer lock part is long so that the space that exists in the inside thereof is large, then when the cap is removed from the liquid drug-expelling part, reduced pressure is created in the space that exists in the inside thereof so that reduced pressure causes leaking of a liquid drug from the syringe. Further, if the outer tubular part is long and the part that closely contacts with the luer lock part is large, then it is inconvenient for a user to remove the cap from the liquid drug-expelling part with ease. Also, if adhesion of the close contact part increases with a time, then it becomes more difficult for the user to remove the cap from the liquid drug-expelling part.

Patent Document 1: Japanese Laid-Open Patent Publication No. 2002-210008

DISCLOSURE OF INVENTION

Problems to be Solved by the Invention

An object of the present invention is to provide a tight-sealing cap for a liquid drug-expelling part in which a length of a contact part between an outer tubular part and a luer lock part is made shorter than that of a contact part between an inner tubular part and a luer nozzle so that this cap can not only minimize the space that creates reduced pressure, which is a cause of leakage of a liquid drug, but is also easy to remove because it is easily twisted off, easily deformable and easily admits air for releasing the vacuum when removed, and that can prevent leaking of a liquid drug from a luer nozzle.

Means for Solving the Problems

In order to solve the above said problems, according to the first invention, there is provided a cap made of an elastic material for tightly sealing a liquid drug-expelling part of a syringe in which a luer nozzle has a gap formed on the outer periphery thereof and a tubular luer lock part is formed on the gap. The tight-sealing cap for liquid drug-expelling part that comprises a thick top surface part that forms an external form, an outer tubular part formed below the outer periphery thereof and an inner tubular part formed below the top surface part of the inside thereof includes the following means.

First, the inner tubular part is formed so that the tip end part of the luer nozzle can be tightly inserted into the same, and the luer nozzle can be tightly sealed at the site of contact between the inner tubular part and the luer nozzle.

Second, the outer tubular part is formed so that it contacts the luer lock part closely therein and can seal the luer lock part tightly at the site of contact between the outer tubular part and the luer lock part.

Third, the length of the site of contact between the outer tubular part and the luer lock part is shorter than the length of the site of contact between the inner tubular part and the luer nozzle.

According to the second invention, there is provided a tight-sealing cap for liquid drug-expelling part in which said outer tubular part in the first invention additionally includes an inclined surface that opens outwardly formed on the lower end part of the inside thereof. According to the third invention, there is provided a tight-sealing cap for liquid drug-expelling part in which the thickness of said outer tubular part in the first or second invention is made thinner than the thickness of said inner tubular part.

Effects of the Invention

According to the present invention, since the length of the contact part between the outer tubular part and the luer lock part is shorter than the length of the contact part between the inner tubular part and the luer nozzle, when the tight-sealing cap is removed from the liquid drug-expelling part, close contact between the outer tubular part and the luer lock part is released before close contact between the inner tubular part and the luer nozzle is released. Thus, since reduced pressure within the luer lock part can be released during a period in which the luer nozzle is tightly sealed, it becomes possible to prevent leakage of a liquid drug from the luer nozzle due to reduced pressure of the luer lock part. At the same time, according to the present invention, when the tight-sealing cap for the liquid drug-expelling part is removed from the liquid drug-expelling part, the tight-sealing cap can be twisted off and deformable easily.

According to the effects of the second and third inventions, since the outer tubular part includes the inclined surface, which is opened outwardly, formed on the lower end part of the inside thereof and it is made thinner than the inner tubular part, when the tight-sealing cap for the liquid drug-expelling part is removed from the liquid drug-expelling part, the tight-sealing cap can be twisted off and deformed more easily and can admit air for releasing reduced pressure more easily.

EXPLANATION OF REFERENCE NUMERALS

Figure 1:
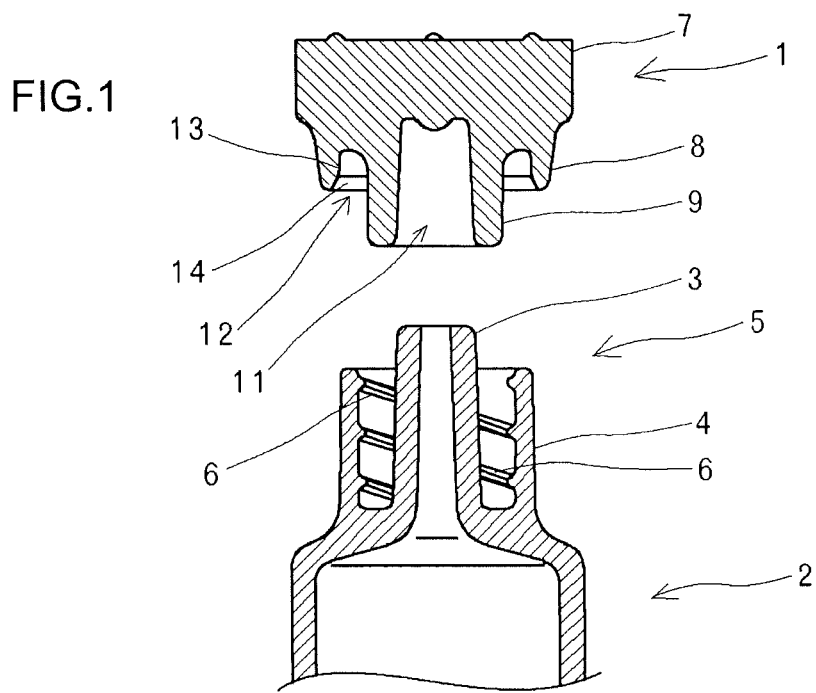
FIG. 1 is an explanatory diagram showing in a cross-sectional fashion a tight-sealing cap and a syringe according to the embodiments.
Figure 2:
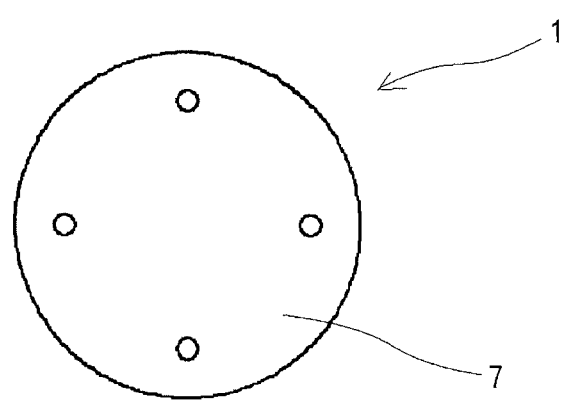
FIG. 2 is a plan view of a tight-sealing cap according to the embodiments.
Figure 3:
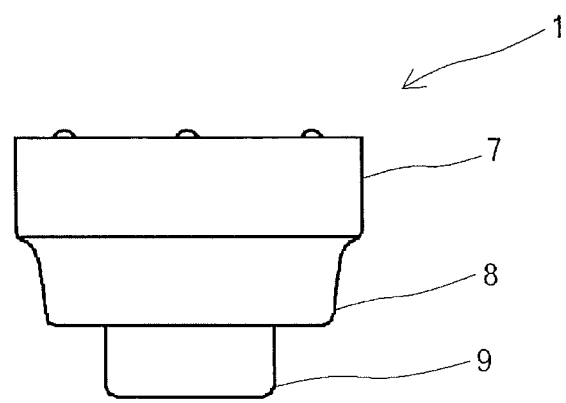
FIG. 3 is a front view showing the same.

1 ... tight-sealing cap
2 ... syringe
3 ... luer nozzle
4 ... luer lock part
5 ... liquid-drug expelling part
6 ... convex spiral projected rim
7 ... top surface part
8 ... outer tubular part
9 ... inner tubular part
10 ... finger
11 ... nozzle insertion gap
12 ... luer lock part insertion gap
13 ... close contact part
14 ... inclined surface

BEST MODE FOR CARRYING OUT THE INVENTION

A mode for carrying out the invention will hereinafter be described with reference to the drawings together with the embodiments. FIG. 1 is an explanatory diagram showing in a cross-sectional fashion a relationship between a tight-sealing cap 1 and a syringe 2 according to the embodiments of the present invention. The syringe 2 to which the present invention can be applied is a syringe made of a resin such as a cyclic olefin resin ("ZEONEX" trade name manufactured by Zeon Corporation, "APEL" trade name manufactured by Mitsui Petrochemical Company, Inc., etc), and a liquid drug-expelling part 5 including a luer nozzle 3 and a luer lock part 4 is formed at a tip end part of the syringe (upper direction in FIG. 1) as shown in FIG. 1.

The luer nozzle 3 and the luer lock part 4 of the liquid drug-expelling part 5 are formed like concentric circles and the luer lock part 4 is formed like a tubular shape of which height is lower than that of the luer nozzle 3. It is needless to say that the present invention can be applied to this tight-sealing cap regardless of a relationship in which the luer nozzle 3 and the luer lock part 4 are the same in height. Further, conversely, the present invention can be applied to this tight-sealing cap even when the luer lock part 4 is higher than the luer nozzle 3.

The luer lock part 4 is erected upright on the outer periphery of the luer nozzle 3 with a gap therebetween. It is customary that a tubular connection part of an injection needle, and an extension tube or the like is screwed and fitted into the gap between the luer nozzle 3 and the luer lock part 4. To this end, a convex spiral projected rim 6 is formed on the inner peripheral surface of the luer lock part 4 according to the embodiments.

The tight-sealing cap 1 is a cap made of an elastic material such as a rubber and this tight-sealing cap is made of a butyl rubber according to the embodiments. Accordingly, if the tight-sealing cap is made thin, then it can be made soft and easy to deform. If on the other hand the tight-sealing cap is made thick, then it can be made hard and easy to press.

Figure 4:
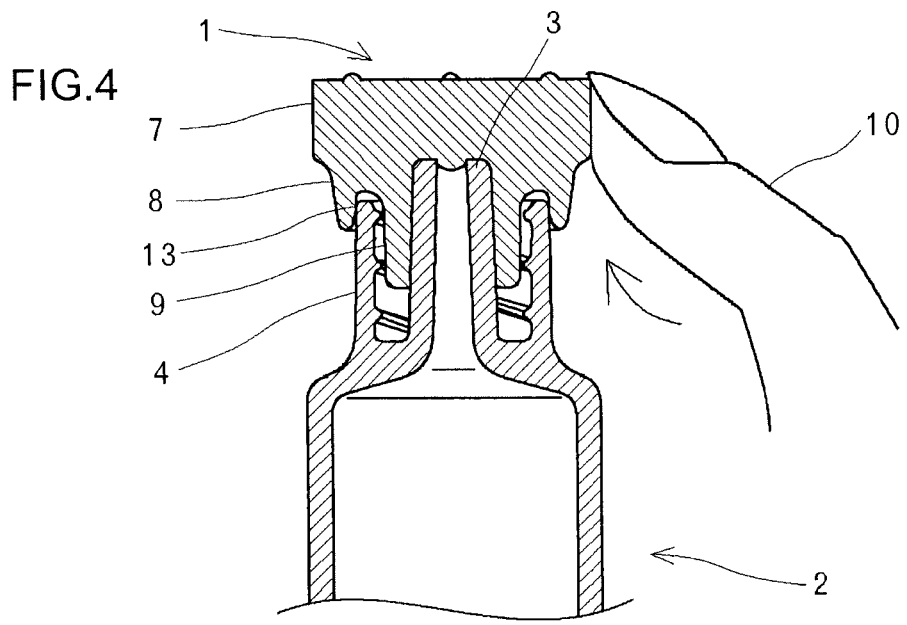
FIG. 4 is an explanatory diagram showing in a cross-sectional fashion the state in which a tight-sealing cap is attached to a liquid drug-expelling part.

The tight-sealing cap 1 comprises a thick top surface part 7 that shapes an external form, an outer tubular part 8 formed below the outer periphery thereof and an inner tubular part 9 formed below the top surface part 7 at the inside thereof. The thickness of the top surface part 7 in the embodiments is 4 mm when the height (length of the upper and lower direction in FIG. 1) of the tight-sealing cap 1 is selected to be 10.5 mm. This height and this thickness are an example. The thickness of the top surface part may be changed variously so long as proper hardness and proper area can be secured when the user twists off the tight-sealing cap 1 and removes the same from the liquid drug-expelling part by pressing upwardly the side surface of the top surface part 7 with a finger 10 as shown in FIG. 4. To be concrete, the thickness of the top surface part 7 may fall within a range of approximately 20 to 50% and should preferably fall within a range of approximately 30 to 40% relative to a height (T) of the tight-sealing cap 1.

A nozzle insertion gap 11 into which the tip end part of the luer nozzle 3 can be closely inserted is formed on the inside of the inner tubular part 9 as shown in FIG. 4. The nozzle insertion gap 11 is shown in FIG. 1. Although the depth of the nozzle insertion gap 11 depends on the height (T) of the tight-sealing cap 1 and the thickness of the top surface part 7, the depth of the nozzle insertion gap may fall within a range of approximately 40 to 80% and should preferably fall within a range of approximately 50 to 70% of the height (T) of the tight-sealing cap 1, for example. The depth of the nozzle insertion gap 11 in the embodiments is selected to be approximately 6.5 mm when the height (height of the upper and lower direction in FIG. 1) of the tight-sealing cap 1 is selected to be to 10.5 mm. In the embodiments, the nozzle insertion gap 11 serves as a contact part between the inner tubular part 9 and the luer nozzle 3.

The inner tubular part 9 is cylinder in shape and it has proper thickness and shape so that the inner tubular part itself can be fitted into the gap between the luer nozzle 3 and the luer lock part 4.

A luer lock part insertion gap 12 is formed on the inside of the outer tubular part 8. The luer lock part insertion gap 12 also is shown in FIG. 1. As shown in FIG. 4, the outer tubular part 8 is made short so long as it is limited to such a length that the outer peripheral surface of the luer lock part 4 can be closely contacted with the inside thereof and that the contact part between the outer tubular part 8 and the luer lock part 4 can tightly seal the liquid drug-expelling part 5, directly, the luer lock part 4.

The length of the site of contact between the outer tubular part 8 and the luer lock part 4 is shorter than the length of the site of contact between the inner tubular part 9 and the luer nozzle 3. That is, a relationship between a length (a) of the site of contact between the inner tubular part 9 and the luer nozzle 3 and a length (b) of the site of contact between the outer tubular part 8 and the luer lock part 4 is selected to be a>b. Here, the length (a) is equivalent to the depth of the aforesaid nozzle insertion gap 11. In the embodiments, the outer tubular part 8 is formed so as to have a length such that a close contact part 13 of approximately 1 mm can be secured near the inside lower end thereof as the site of contact between it and the outer peripheral surface of the luer lock part 4. This length of the outer tubular part is a length by which vapor or moisture can be prevented from entering into the luer lock part 4, and it was determined based on experimental results because the length of the close contact part between an inner surface of a syringe of an injector and gasket peak formed on a cylindrical surface of a plunger thereof is approximately 1 mm to keep in liquid tight therebetween. A length (c) of the close contact part 13 is equal to or less than a depth (d) of the luer lock part insertion gap 12 (d≧c). Since the luer lock part 4 need not be fitted into the deepest part of the luer lock part insertion gap 12 and the tip end portion of the luer nozzle 3 may be closely inserted into the luer lock part insertion gap, a very small space may be provided between the tip end portion of the luer lock part 4 and the deepest portion of the insertion gap 12. Also, as will be described later on, when an inclined surface 14 that opens outwardly is formed on the lower end part of the inside of the outer tubular part 8, the outer peripheral surface of the luer lock part 4 does not contact with the inclined surface 14. The length of the close contact part 13 is not limited to the length of approximately 1 mm in the embodiments and this length is determined in consideration of the above-described conditions, the lengths of the luer nozzle 3 and the luer lock part 4 and conditions of a heating and sterilizing treatment. The length of the close contact part 13 generally falls within a range of from 1±0.1 to 0.2 mm.

While the close contact part between the close contact part 13 and the outer peripheral surface of the luer lock part 4 is in a surface-contact fashion in the illustrated embodiments, the present invention is not limited thereto and protrusions formed on the luer lock part 4 and the close contact part 13 may contact with the close contact part 13 of the opposing outer tubular part 8 or the outer peripheral surface of the luer lock part 4.

Further, the outer tubular part 8 has at the lower end portion of the inside thereof formed an inclined surface 14 that opens outwardly. The inclined surface 14 in the embodiments opens outwardly with an angle of 25 degrees (angle relative to the inner vertical surface of the outer tubular part 8). Owing to the existence of this inclined surface 14, when the luer lock part is inserted into the tight-sealing cap 1, this inclined surface can play a role of a guiding member so that the luer lock part can be inserted into the tight-sealing cap more easily. At the same time, when a user pushes the top surface part 7 of the tight-sealing cap 1 in the oblique upper direction with the finger 10 as shown in FIG. 4, the outer tubular part 8 can be easily removed from the luer lock part 4. Insofar as the existence of the inclined surface 14 can fulfill such functions, the aforesaid angle of the inclined surface 14 is not limited to 25 degrees but it can be changed in a range of from about 5 to 45 degrees.

The side wall of the outer tubular part 8 is made thinner than the side wall of the inner tubular part 9. It is sufficient for the outer tubular part 8 to tightly seal therein the outer periphery of the luer lock part 4. If the outer tubular part is made thinner, when a user pushes the top surface part 7 of the tight-sealing cap 1 in the oblique upper direction with the finger 10 as shown in FIG. 4, the outer tubular part 8 can be deformed easily. When the outer tubular part is deformed, the outer tubular part can be easily removed from the luer lock part 4 and it can admit air easily. The thickness of the side wall of the outer tubular part 8 may fall within a range of approximately 25 to 75% and should preferably fall within a range of approximately 40 to 60% of the thickness of the side wall of the inner tubular part 9.

The invention claimed is:

1. A tight-sealing cap made of an elastic material for tightly sealing a liquid drug-expelling part of a syringe in which a tubular luer lock part is installed to form a gap around an outer periphery of a luer nozzle, the tight-sealing cap comprising:
   a thick top surface part providing an external form, said top surface part having a thickness (D),
   an outer tubular part formed below an outer periphery of said thick top surface part, the outer tubular part having a tip end, and
   an inner tubular part formed below said top surface part at the inside of and separate from said outer tubular part, the inner tubular part having a tip end,
   wherein:
   said inner tubular part is formed such that a tip end portion of said luer nozzle is tightly insertable into said inner tubular part such that said inner tubular part tightly seals said luer nozzle at a contact site between said inner tubular part and said luer nozzle;
   said outer tubular part is formed such that said luer lock part closely contacts with the inside of said outer tubular part, such that said outer tubular part tightly seals said luer lock part at a contact site between said outer tubular part and said luer lock part;
   the tip end of said inner tubular part is arranged to protrude in a longitudinal direction relative to the tip end of said outer tubular part
   a length at the contact site between said outer tubular part and said luer lock part is shorter than a length at the contact site between said inner tubular part and said luer nozzle; and
   said tight-sealing cap has a height (T), and wherein a ratio of D/T is between 0.20 to 0.50.

2. A tight-sealing cap for the liquid drug-expelling part of a syringe according to claim 1, wherein a length at the contact site between said inner tubular part and said luer nozzle is (a), and a ratio of a/T is between 0.40 to 0.80.

3. A tight-sealing cap for the liquid drug-expelling part of a syringe according to claim 1, wherein a thickness of a side wall of said outer tubular part is smaller than a thickness of a side wall of said inner tubular part, and the thickness of the side wall of said outer tubular part is between 25 to 75% of the thickness of the side wall of said inner tubular part.

4. A tight-sealing cap for the liquid drug-expelling part of a syringe according to claim 1, wherein an outer diameter of said outer tubular part is smaller than an outer diameter of said top surface part, so that a slanting part is formed at a connection site between an outer peripheral surface of said top surface part and an outer peripheral surface of said outer tubular part.

* * * * *

UNITED STATES PATENT AND TRADEMARK OFFICE
CERTIFICATE OF CORRECTION

PATENT NO. : 8,529,519 B2 Page 1 of 1
APPLICATION NO. : 12/935638
DATED : September 10, 2013
INVENTOR(S) : Hasegawa et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 245 days.

Signed and Sealed this
Fifteenth Day of September, 2015

Michelle K. Lee
*Director of the United States Patent and Trademark Office*